(12) United States Patent
Rodriguez et al.

(10) Patent No.: US 12,343,421 B2
(45) Date of Patent: Jul. 1, 2025

(54) VITAMIN D BASE LAYER

(71) Applicant: Solaana MD LLC, Framingham, MA (US)

(72) Inventors: Madeline Costello Rodriguez, Dover, MA (US); Rosalynn Melanie Nazarian, Wellesley, MA (US)

(73) Assignee: Solaana MD LLC, Framingham, MA (US)

( * ) Notice: Subject to any disclaimer, the term of this patent is extended or adjusted under 35 U.S.C. 154(b) by 17 days.

(21) Appl. No.: 17/453,095

(22) Filed: Nov. 1, 2021

(65) Prior Publication Data
US 2023/0133004 A1    May 4, 2023

(51) Int. Cl.
*A61K 8/67* (2006.01)
*A61K 8/92* (2006.01)
*A61K 8/9789* (2017.01)
*A61Q 17/04* (2006.01)

(52) U.S. Cl.
CPC .............. *A61K 8/67* (2013.01); *A61K 8/92* (2013.01); *A61K 8/9789* (2017.08); *A61Q 17/04* (2013.01)

(58) Field of Classification Search
None
See application file for complete search history.

(56) References Cited

U.S. PATENT DOCUMENTS

| 2,118,566 | A  | * | 5/1938 | De Wayne | A61K 8/24 510/130 |
| 2017/0014332 | A1 | * | 1/2017 | Gerardi | A61K 8/04 |

FOREIGN PATENT DOCUMENTS

| CN | 107108837 | B  | * | 4/2021 | ............ | A61K 47/34 |
| EP | 0998925 | A1 | * | 5/2000 | | |
| EP | 2859886 | A1 | * | 4/2015 | ............ | A61K 31/573 |
| FR | 2978043 | A1 | * | 1/2013 | ............... | A61K 8/97 |
| FR | 3058057 | A1 | * | 5/2018 | ............... | A61K 8/36 |
| JP | H1053527 | A  | * | 2/1998 | | |
| KR | 20200033689 | A  | * | 3/2020 | | |
| WO | 20110068667 | A  | * | 6/2011 | | |
| WO | WO-2013103944 | A1 | * | 7/2013 | ............ | A61K 36/886 |

OTHER PUBLICATIONS

CN-107108837-B, PE2E machine translation, Apr. 2021 (Year: 2021).*
EP-0998925-A1, PE2E machine translation, May 2000 (Year: 2000).*
FR-3058057-A1, PE2E machine translation, May 2018 (Year: 2018).*
FR-2978043-A1, PE2E machine translation, Jan. 2013 (Year: 2013).*
Greenville, What is RBD Coconut Oil, May 1, 2019. https://greenville-agro.com/blog/what-is-rbd-coconut-oil/ (Year: 2019).*
JP-H1053527-A PE2E machine translation, Feb. 1998 (Year: 1998).*
KR-20200033689-A, PE2E machine translation, Mar. 2020 (Year: 2020).*
Christopoulou et al., Rosemary Extract and Essential Oil as Drink Ingredients: An Evaluation of Their Chemical Composition, Genotoxicity, Antimicrobial, Antiviral, and Antioxidant Properties, Foods 2021, 10, 3143. https://doi.org/10.3390/foods10123143 (Year: 2021).*
Machine Translation of KR-20110068667 (Year: 2011).*
PubMed, Calcitriol and Alfacalcidol, retrieved online Jun. 25, 2024 (Year: 2024).*
Zhou et al., Effects of calcitriol on random skin flap survival in rats, Scientific Reports | 6:18945 | DOI: 10.1038/srep18945, Published: Jan. 6, 2016 (Year: 2016).*
Rizka et al., Effect of Alfacalcidol on Inflammatory markers and T Cell Subsets in Elderly with Frailty Syndrome: a Double Blind Randomized Controlled Trial, Acta Med Indones—Indones J Intern Med • vol. 50 • No. 3 • Jul. 2018 (Year: 2018).*

* cited by examiner

*Primary Examiner* — Jennifer A Berrios
(74) *Attorney, Agent, or Firm* — Schwegman Lundberg & Woessner, P.A.

(57) ABSTRACT

A composition of matter which promotes vitamin D absorption through a cosmetically acceptable composition formulated using fat soluble vitamin D3 (cholecalciferol) added to a cosmetically acceptable composition that comprises RBD coconut oil.

5 Claims, No Drawings

VITAMIN D BASE LAYER

BACKGROUND

Vitamin D is a group of fat-soluble secosteroids responsible for increasing intestinal absorption of calcium, magnesium, and phosphate, and many other biological effects. In humans, the most important compounds in this group are vitamin D3 (also known as cholecalciferol) and vitamin D2 (ergocalciferol). The major natural source of the vitamin is synthesis of cholecalciferol in the lower layers of skin epidermis through a chemical reaction that is dependent on sun exposure (specifically UVB radiation).

While the major source of natural Vitamin D synthesis occurs through a chemical reaction dependent upon sun exposure, medical organizations such as the American Cancer Society recommend the use of sunscreen because it aids in the prevention of skin malignancies, such as squamous cell carcinomas. Sunscreen (and sunblock) prevents ultraviolet light from reaching the skin, and even moderate protection can substantially reduce vitamin D synthesis. As a result, concerns have been raised about a reduction in vitamin D synthesis, as well as potential vitamin D deficiency arising from prolonged use of sunscreen.

SUMMARY OF INVENTION

An object of the disclosed invention is to provide a composition that promotes vitamin D absorption into the skin, while also allowing an individual to use sunscreen or sunblock to prevent excessive UV radiation. The present invention therefore provides a method of supplementing vitamin D through a low-viscosity, or semi-solid, topical preparation intended for application to the skin as a base-layer before application of a typical sunscreen or sunblock. According to one embodiment, a base layer is formulated through the addition of vitamin D to a cosmetically acceptable composition that comprises coconut oil, rosemary extract, and coriander extract.

DETAILED DESCRIPTION

According to traditional beliefs, hepatic and renal activation of vitamin D are necessary to produce calcitriol. However, it has been known for many years that the skin is capable of converting vitamin D to calcitriol on its own, in addition to creating vitamin D through exposure to sunlight. Accordingly, the disclosed invention provides a topical supplement to promote and maximize vitamin D absorption, which may be applied directly to the skin as a base layer to be added before sunscreen or sunblock.

The present invention is a composition of matter which promotes vitamin D absorption through a cosmetically acceptable composition that comprises a solid fat, such as refined, bleached, and deodorized (RBD) coconut oil. More specifically, a base layer is formulated using fat soluble vitamin $D_3$ (cholecalciferol) or other biologically active vitamin D derivatives which is added to a cosmetically acceptable composition that comprises RBD coconut oil. An individual may thereby apply the base layer directly to their skin before the application of sunscreen. Thus, when the individual applies the sunscreen on top of the base layer, the sunscreen inhibits UV radiation and its cancer-causing effects, while the vitamin $D_3$ is readily, and more effectively, absorbed into the skin due to the presence of the solid refined fat. Thus, the benefits of vitamin D formation from UV radiation can be achieved without the harmful exposure.

It is an object of this invention to provide a cream or lotion which is easy to apply and which is smooth and velvety to the touch. Accordingly, in certain embodiments the composition may be fortified with emulsifying agents which facilitate mixing of the oil and water phases and give the product a creamy consistency.

It is another object of this invention to provide a product which is stable and has a long shelf-life. Accordingly, the composition may include one or more different preservatives, each of which contributes to enhanced stability.

It is a further object of this invention that this product is a semi-solid or low-viscosity cream or lotion which may be easily handled and applied by an individual. Accordingly, the composition may include one or more thickening agents, each of which may confer enhanced gel-like properties to the resultant mixture.

It is yet a further object of this invention to provide a mixture which facilitates the uptake of vitamin D by the skin. Accordingly, the composition contains coriander seed extract, which contains high levels of magnesium. Studies have shown that magnesium is absorbed transdermally and may increase vitamin D absorption when taken together.

It is still further an object of this invention to help moisturize the skin, in order to increase vitamin D absorption. Accordingly, the composition contains a carrier base oil or butter, such as one or more of: RBD coconut oil; shea butter; sunflower seed oil; jojoba seed oil; neem seed oil; rosehip oil; wheat germ oil; carrot seed oil; primrose oil; argan oil; grapeseed oil; tea tree oil; safflower oil; sesame seed oil; prickly pear oil; camellia oil; avocado oil; and any combination thereof.

According to certain embodiments, the composition according to the invention comprises a derivative of vitamin D, (i.e., cholecalciferol) chosen from: 1-hydroxycholecalciferol; 1.25-dihydroxycholecalciferol; and mixtures thereof. The concentration of vitamin D which is present in the composition according to the invention may be based on a minimum daily value. The effective amount may vary from subject to subject but will generally lie within the range of from 0.00001 to 20%, preferably from 0.001 to 10% by weight of the composition. In some embodiments, the composition is formulated such that 1 tablespoon of the composition contain 5 mcg of vitamin D.

In certain embodiments, whether in the form of $D_2$ or $D_3$, the molecular weight of vitamin D utilized in the composition comprises a molecular weight less than 500 Dalton (g/mol), in order to maximize absorption in human skin.

According to certain embodiments, the composition may comprise an emulsifying wax. Emulsifying wax is created when a wax material (either a vegetable wax of some kind or a petroleum-based wax) is treated with a detergent (typically sodium dodecyl sulfate or polysorbates) to cause it to make oil and water bind together into a smooth emulsion. The ingredients for emulsifying wax may include cetearyl alcohol and a polyoxyethylene derivative of a fatty acid ester of sorbitan (a polysorbate).

According to certain embodiments, the composition may comprise stearic acid. Stearic acid is a saturated fatty acid with an 18-carbon chain, and is less likely to be incorporated into cholesterol esters. In epidemiologic and clinical studies, stearic acid was found to be associated with lowered LDL cholesterol in comparison with other saturated fatty acids.

According to certain embodiments, the composition may comprise coconut oil. Coconut oil is an edible oil derived from the wick, meat, and milk of the coconut palm fruit. Due to its lipophilicity/lipophilicy properties (fat-soluble), vitamin D is readily dissolved in coconut oil.

In some example embodiments, the preferred proportions of the composition are as follows:

Emulsifying Wax at a weight percent of between 4-6%, and in a preferred embodiment of 5.41000%;

Stearic Acid (Palm Derived) at a weight percent of 4-6%, and in a preferred embodiment of 4.95000%;

Coconut Oil RBD at a weight percent of 23-26%, and in a preferred embodiment of 25.22000%;

Arrowroot Power at a weight percent of 0.25-0.75%, and in a preferred embodiment of 0.49000%;

Deionized Water at a weight percent of 55-65%, and in a preferred embodiment of 59.90000%;

Aloe Vera 200:1 Powder at a weight percent of 0.005-0.020%, and in a preferred embodiment of 0.01000%;

Citric Acids at a weight percent of 0.05-0.10%, and in a preferred embodiment of 0.09000%;

Tetrasodium Glutamate Diacetate at a weight percent of 0.4-0.7%, and in a preferred embodiment of 0.53000%;

Vegetable Glycerin at a weight percent of 1-3%, and in a preferred embodiment of 1.95000%;

Hyaluronic Acid Powder at a weight percent of 0.01-0.04%, and in a preferred embodiment of 0.02000%;

Xanthan Gum at a weight percent of 0.09-0.3%, and in a preferred embodiment of 0.12000%;

Phenoxyethanol at a weight percent of 0.25-1.5%, and in a preferred embodiment of 1.00000%;

Alcohol at a weight percent of 0.09-0.25%, and in a preferred embodiment of 0.15000%;

Passion Fruit Fragrance Oil at a weight percent of 0.009-0.03%, and in a preferred embodiment of 0.01000%;

Coriander Seed Essential Oil at a weight percent of 0.009-0.03%, and in a preferred embodiment of 0.01000%;

Rosemary extract at a weight percent of 0.009-0.03%, and in a preferred embodiment of 0.01000%;

Sweet Orange Essential Oil at a weight percent of 0.01-0.04%, and in a preferred embodiment of 0.02000%;

Mint Essential Oil at a weight percent of 0.05-0.15%, and in a preferred embodiment of 0.10000%; and Liquid Vitamin D at a weight percent of 0.01-0.03%, and in a preferred embodiment of 0.02000%.

According to certain embodiments, the composition may be manufactured through a process by which the emulsifying wax, stearic acid and coconut oil are melted together at a temperature of between 150 F-160 F to provide a melt phase. The mixture may then be removed from heat. Arrowroot powder is then added to the mixture and mixed till fully dissolved.

A water phase is prepared using deionized water, Aloe Vera 200:1 powder, citric acid, and tetrasodium glutamate diacetate heated together at a temperature of 135 F-140 F. The vegetable glycerin, hyaluronic acid powder, xanthan gum, and phenoxyethanol are premixed with one another, and then high sheared into the water phase.

The water phase and the melt phase are then high sheared together and blended until smooth. Once the mixture is cooled to 110 F or lower, the alcohol, passion fruit fragrance oil, coriander seed essential oil, sweet orange essential oil, mint essential oil, and liquid vitamin D are added. The pH is then adjusted to 4.2-5.8 using citric acid or baking soda.

According to certain embodiments, the composition may include rosemary extract. Rosemary extracts have attracted attention because they contain secondary metabolites with therapeutic potential, such as: tricyclic diterpenes, such as carnosol and carnosic; phenolic acids such as rosmarinic and caffeic acid; triterpenes such as ursolic and oleanolic acid; micromeric acids; and essential oils. These compounds have been applied topically and studied for their anti-inflammatory capacity, wound-healing potential, effects on tissue survival, anti-skin-cancer effects, antinociceptive effects, antifungal effects, and UV-protective activity. Topical administration strategies of such compounds avoid first-pass metabolism, releasing the drug at the site of action and resulting in a lower risk of side effects. This strategy can be applied to improve the properties of cosmetic products (e.g., those that combat UV exposure, aging, and cellulite), owing to the anti-inflammatory activity and free radical-scavenging effects of *Rosmarinus officinalis*.

Research also indicates that monoterpertenes, presented in rosemary oil and extract, promote cutaneous absorption, and enhance penetration. The effect of rosemary oil on the permeation of aminophylline was determined in human skin in vivo using attenuated total reflection Fourier transform infrared spectroscopy. Rosemary oil and extract were found to enhance the permeation of aminophylline. Accordingly, in certain embodiments, the composition may include rosemary extract in order to increase and promote absorption of vitamin D into the skin.

What is claimed is:

1. A topical supplement formulated as an emulsion with a low-viscosity in order to be applied as a base layer upon human skin before sunscreen to promote vitamin D absorption, the topical supplement consisting of:

coconut oil in an amount of 23-26% of a total weight of the emulsion;

coriander seed extract present in an amount of 0.009-0.03% of the total weight of the emulsion;

aloe vera powder present in an amount of 0.005-0.02% of the total weight of the emulsion;

a vitamin D derivative, present in an amount of 0.001 to 10% of the total weight of the emulsion, wherein the vitamin D derivative comprises a mixture of 1-hydroxycholecalciferol and 1.25-dihydroxycholecalciferol having a molecular weight below 500 Dalton to maximize absorption of the vitamin D derivative into the human skin;

deionized water present in an amount of 55-65% of the total weight of the emulsion;

an emulsifying wax present in an amount of 4-6% of the total weight of the emulsion, wherein the emulsifying wax comprises cetearyl alcohol and a polyoxyethylene derivative of a fatty acid ester of sorbitan;

a preservative to enhance stability and shelf-life of the composition;

rosemary oil derived monoterpenes to promote cutaneous absorption and enhance penetration of the topical supplement into the human skin, wherein the rosemary oil derived monoterpenes are present in an amount of 0.009-0.03% of the total weight of the emulsion; and wherein the emulsion comprises an oil phase and a water phase, with the coconut oil and the coriander seed extract present in the oil phase, and the deionized water and the aloe vera present in the water phase.

2. The topical supplement of claim 1, wherein the coconut oil comprises RBD coconut oil.

3. The topical supplement of claim 1, wherein the topical supplement comprises a pH of 4.2 to 5.8.

4. The topical supplement of claim 1, wherein the aloe vera powder is present at 0.01000% of a total weight of the topical supplement.

5. The topical supplement of claim 1, wherein the aloe vera powder comprises aloe vera 200:1 powder.

* * * * *